United States Patent
Manzer et al.

(10) Patent No.: US 6,600,081 B2
(45) Date of Patent: Jul. 29, 2003

(54) PROCESS FOR THE PREPARATION OF P-XYLENE

(76) Inventors: Leo E. Manzer, 714 Burnley Rd., Wilmington, DE (US) 19898; Kostantinos Kourtakis, 501 N. Orange St. #C1, Media, PA (US) 19063; Norman Herron, 408 Apple Rd., Newark, DE (US) 19711-5118; Eugene M. McCarron, 3940 Centerville Rd., Greenville, DE (US) 19807; Paul D. Ver Nooy, 429 Dogwood Dr., Hockessin, DE (US) 19707

(*) Notice: Subject to any disclaimer, the term of this patent is extended or adjusted under 35 U.S.C. 154(b) by 0 days.

(21) Appl. No.: 09/808,660

(22) Filed: Mar. 15, 2001

(65) Prior Publication Data

US 2002/0007100 A1 Jan. 17, 2002

Related U.S. Application Data

(60) Provisional application No. 60/189,773, filed on Mar. 16, 2000.

(51) Int. Cl.$^7$ ............................. C07C 2/52; C07C 15/00
(52) U.S. Cl. ...................... 585/322; 585/315; 585/407; 585/418; 585/420
(58) Field of Search ................................. 585/407, 418, 585/420, 421, 322, 315

(56) References Cited

U.S. PATENT DOCUMENTS

| | | | |
|---|---|---|---|
| 3,202,725 A | 8/1965 | Lorz et al. ............... | 260/673.5 |
| 3,836,603 A | 9/1974 | Conner, Jr. et al. ...... | 260/673.5 |
| 3,937,748 A | * 2/1976 | Miklas ........................ | 585/433 |
| 5,877,372 A | * 3/1999 | Evans et al. ................. | 585/510 |

* cited by examiner

Primary Examiner—Thuan D. Dang

(57) ABSTRACT

The present invention relates to a process for the preparation of para-xylene from trimethylpentane.

10 Claims, 1 Drawing Sheet

PROCESS FOR THE PREPARATION OF P-XYLENE

This application claims the benefit of provisional application No. 60/189,773 filed Mar. 16, 2000

FIELD OF THE INVENTION

The present invention relates to the dehydrocyclization of trimethylpentane and trimethylpentenes to p-xylene using chromium-containing catalysts.

BACKGROUND

Para-xylene is a useful aromatic material, especially for the production of terephthalic acid, a polyester monomer. It is desirable to produce para-xylene in relatively high yields. Manufacture of aromatic hydrocarbons from acyclic alkanes or acyclic alkenes is well known in the art. For example, U.S. Pat. No. 3,202,725 discloses a process for the manufacture of xylenes containing greater than 95% of the commercially desirable para isomer. The process comprises of feeding to a catalytic dehydrogenation zone various hydrocarbon feeds which include isooctane, diisobutylene, and a mixture of isobutane and isobutylene. The dehydrogenation catalyst comprises 15 to 25% chromium oxide ($Cr_2O_3$) on an alumina support composed essentially of eta-alumina. The yield of para-xylene per-pass in the aromatization step is low because of the ease with which the trimethylpentenes are cracked to isobutylene under the reaction conditions. A large recycle stream of the isobutylene is required to be sent back to an acid dimerization step to produce additional trimethylpentane.

The primary commercial source of low molecular weight aromatics (i.e., benzene, toluene, and xylenes) is extraction from catalytic reformate, which is produced in petroleum refining for making high-octane gasoline. Reformate may contain from 20 to 30 percent of $C_6$ to $C_8$ aromatics. High purity aromatics can be removed only by selective extraction because of the overlapping boiling points of these aromatics with other hydrocarbons present in the reformate. Such processes are complex and costly. Isolation of para-xylene adds further complexity. Separation of para-xylene from its isomers is usually done in one of two ways. The more recent method is to use an elaborate multi-valve absorption process using molecular sieves. An older method, still used, is multi-stage fractional crystallization at low temperatures to recover a pure para-xylene fraction.

Another major problem with the separation schemes described above is that the para-xylene isomer of the three possible xylenes is only present in about 20% of the equilibrium mixture. Hence, large volumes of undesired materials are passed through either of the above separation processes to obtain the relatively minor amounts of para-xylene present.

There is a need for an efficient process for the production of para-xylene that avoids the current costly and elaborate separation procedures.

SUMMARY OF THE INVENTION

The present invention discloses a process for the manufacture of xylene from 2,2,4-trimethylpentane, comprising: (a) feeding to a reactor a reactor feed comprising 2,2,4-trimethylpentane and a diluent gas selected from the group consisting of nitrogen, methane, ethane, propane, and mixtures thereof wherein the molar concentration of 2,2,4-trimethylpentane to said diluent gas is about 50% or less; (b) contacting in the vapor phase said reactor feed in said reactor with a catalyst comprising chromium to produce a reactor effluent containing xylene and by-products containing 2,2,4-trimethlypentene, isobutane, and isobutylene, and unreacted 2,2,4-trimethylpentane; and (c) optionally, separating xylene from said by-products, unreacted 2,2,4-trimethylpentane, and diluent gas.

DETAILED DESCRIPTION

Figure 1:
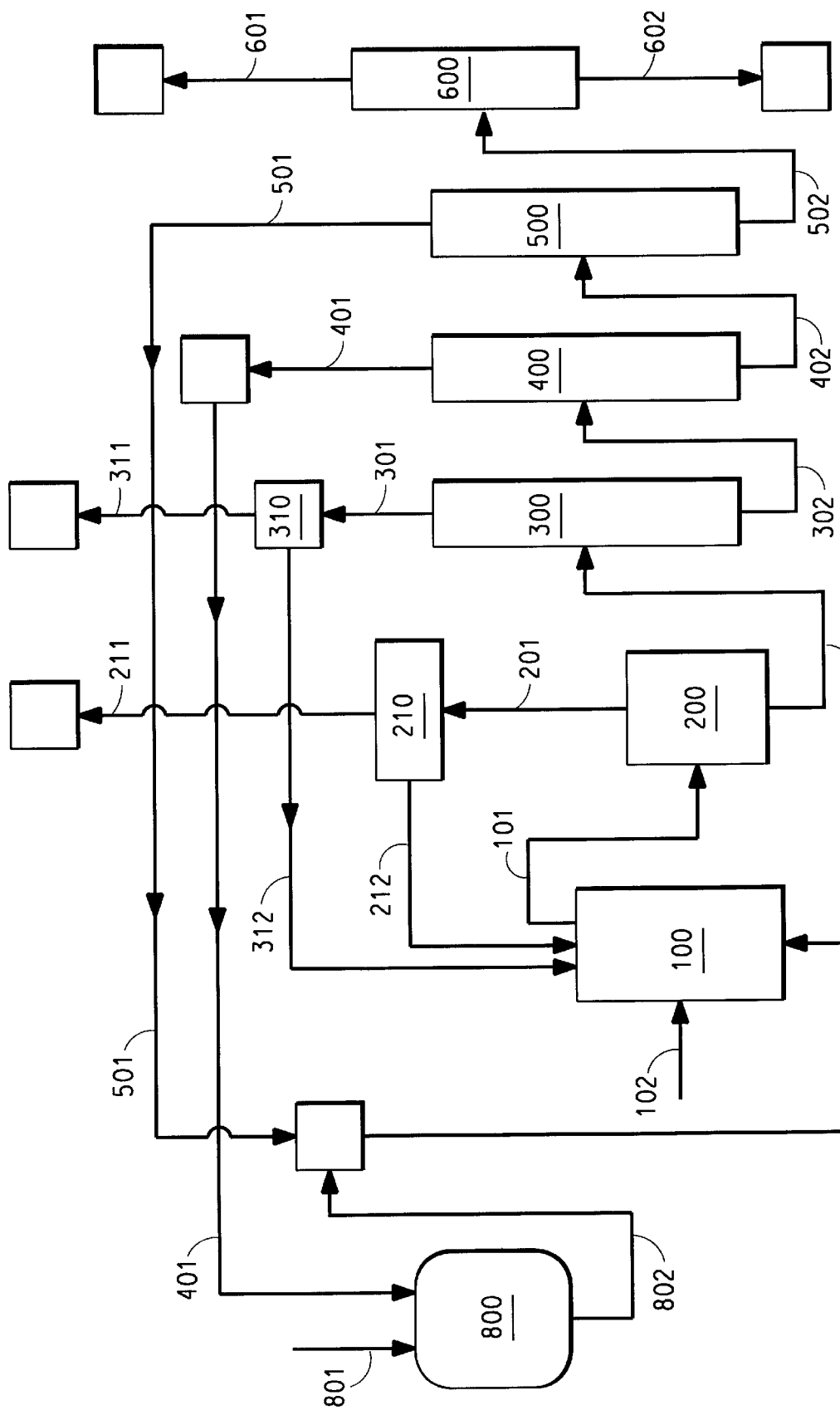
FIG. 1 is a schematic flow diagram of an embodiment of this invention.

This invention provides a process for the manufacture of p-xylene from 2,2,4-trimethylpentane. The process is preferably done in a series of steps. A first step involves feeding to a reactor feed comprising 2,2,4-trimethylpentane, and a diluent gas selected from the group consisting of nitrogen, methane, ethane, propane and mixtures thereof wherein the molar concentration of 2,2,4-trimethylpentane to said diluent gas is about 50% or less and then contacting, in the vapor phase, the reactor feed with a catalyst comprising chromium to produce a reaction effluent which comprises xylene, 2,2,4-trimethylpentene, isobutane, isobutylene, and unreacted 2,2,4-trimethylpentane. The xylene of the first step comprises isomers of xylene, including para-xylene. A second step includes separating from the effluent hydrogen and $C_1$, $C_2$, and $C_3$ hydrocarbons. A third step entails further separating from the effluent isobutane, isobutylene, 2,2,4-trimethylpentenes, and unreacted 2,2,4-trimethylpentane to provide an aromatics fraction consisting of benzene, toluene, and xylenes and a fraction (A) consisting of 2,2,4-trimethylpentenes and 2,2,4-trimethylpentane. A fourth step comprises dimerizing the recovered isobutane and isobutylene in a separate reaction zone to obtain additional 2,2,4-trimethylpentane and 2,2,4-trimethylpentenes. A fifth step embodies feeding the fourth-step products to the first-step reactor. A sixth step comprises recycling fraction (A) to the first-step reactor. A seventh step comprises recovering from the third step the aromatics fraction of xylenes, wherein the p-xylene concentration is 95% or greater of the xylenes fraction.

The catalyst of this invention comprises chromium, preferably supported. The chromium catalysts can be promoted or treated with metals selected from the group consisting of iron, tin, and tungsten. Preferably, the catalyst also contains at least one metal from Groups 1 and 2 (i.e., Na, K, Rb, Cs, Mg, Ca, Sr, and Ba).

The catalyst components are combined with a refractory inorganic oxide support material, in particular, alumina (especially eta-alumina) and zirconia. The metal(s) can be combined or intimately associated with a porous inorganic support or carrier by various known-art techniques such as ion-exchange, coprecipitation with the support (e.g., alumina) in the sol or gel form, and the like. For example, the catalyst combination can be formed by adding together suitable reagents such as salts of the required metal(s) and ammonium hydroxide or ammonium carbonate, and a salt of aluminum such as aluminum chloride or aluminum nitrate to form aluminum hydroxide. The aluminum hydroxide containing the salts can then be treated with the alkali or alkaline earth, heated, dried, formed into pellets or extruded, and then calcined.

Alternatively, the metal(s) can be deposited on a previously pilled, pelleted, beaded, extruded, or sieved particulate support material by the impregnation technique. Porous refractory inorganic oxides in dry or solvated state are contacted, either alone or admixed, or otherwise incorporated with a metal or metal-containing solution or solutions. Impregnation is achieved by either the incipient wetness technique or a technique using absorption from a dilute or concentrated solution(s) with subsequent filtration or evaporation to effect total uptake of the metallic components.

In combining the metals with the support, virtually any soluble compound of the respective metal can be used, but a soluble compound which can be easily thermally decomposed is preferred, such as inorganic salts of carbonates, bicarbonates, nitrates, inorganic complex compounds, or organic salts such as a complex salt of acetylacetone, an amine salt, or the like.

2,2,4-Trimethylpentane (TMP) is diluted with a gas selected from the group consisting of nitrogen, methane, ethane, propane, and mixtures thereof, such that the molar concentration of TMP in the reactor feed is about 50% or less, preferably the molar concentration of TMP is about 20%, most preferably about 10%. The diluted TMP feed is contacted with a catalyst comprising chromium in a dehydrogenation reactor. The reactor effluent is sent to a flash drum or other liquid-vapor separation system wherein hydrogen and low molecular weight gases ($C_1$ to $C_3$ hydrocarbons) are separated overhead, while the unvaporized products are withdrawn as a liquid. The liquid products are sent to a fractional distillation column where isobutane and isobutylene are removed overhead and the unvaporized higher boiling materials are discharged to another fractional distillation column. In this second column TMP and a mixture of 2,2,4-trimethylpentene-1 (TMPE-1) and 2,2,4-trimethylpentene-2 (TMPE-2) are removed overhead and the unvaporized higher boiling materials are sent to an aromatics fractional distillation column (3). In this third column toluene and benzene are removed overhead and unvaporized aromatics that are recovered comprise greater than 95% para-xylene, preferably greater than 98% para-xylene with the remainder consisting essentially of the other xylene isomers. The TMP, TMPE-1, and TMPE-2 that are recovered overhead from the second column are recycled to the dehydrogenation reactor.

The isobutane and isobutylene recovered in the third step are sent to a dimerization reactor where a mixture of TMP, TMPE-1, and TMPE-2 are prepared. Any suitable known process may be used in the dimerization reactor. For example, isobutane and isobutylene may be passed over a dimerization catalyst (for example, silica-alumina) at moderate temperatures and pressures and high throughputs. Typical operations for a silica-alumina catalyst involve temperatures of about 150° C. to about 200° C., pressures of about 2200 kPa to about 5600 kPa, and liquid hourly space velocities of about 3 to 10. Other known dimerization processes use either hydrogen fluoride or sulfuric acid catalysts. In order to favor alkylation rather than polymerization of the olefin, isobutane concentration should be kept as high as possible. With the use of the latter two catalysts, reaction temperatures are kept low (generally from about 15° C. to about 50° C. with hydrogen fluoride and from about 5° C. to about 15° C. with sulfuric acid) to ensure high levels of conversion. The dimerization products which consist essentially of TMP, TMPE-1, and TMPE-2 together with some triisobutylenes are recycled to the dehydrogenation reactor.

FIG. 1 illustrates one method of practicing this invention. With reference to this figure, a feed comprising 2,2,4-trimethylpentane is passed through line (802) into a dehydrogenation reactor (100) containing a catalyst comprising chromium. Another feed comprising 2,2,4-trimethylpentane and 2,2,4-trimethylpentenes is passed through line (501) into reactor (100). Methane, and ethane diluent gas, and optionally nitrogen, is passed through line (212) into reactor (100). Propane and propylene diluent gas is passed through line (312) into reactor (100). Optionally, nitrogen diluent gas is passed through line (102) into reactor (100). The reactor effluent is sent through line (101) to a flash drum or other liquid-vapor separator system (200). A gas stream comprising hydrogen, methane, ethane, and optionally nitrogen is removed overhead through line (201) into a gas separation unit (210) wherein some of the methane and ethane is sent to reactor (100) through line (212). Hydrogen and the remainder of the ethane and methane are purged through line (211). The unvaporized products are withdrawn as liquid through line (202).

The liquid products are first sent to a depropanizer (300), which is preferably a fractionating column, and wherein propane and propylene are removed overhead through line (301) into a gas separation unit (310) wherein part of the propane and propylene is optionally sent to reactor (100) through line (312). The remainder of the propane and propylene is purged through line (311). The unvaporized products are withdrawn as liquid through line (302) and sent to a debutanizer (400), which is also preferably a fractionating column, wherein isobutane and isobutene are removed overhead through line (401) and sent to alkylation reactor (800). Fresh isobutane is sent to alkylation reactor (800) through line (801). The unvaporized products are withdrawn as liquid through line (402) and sent to a fractionating column (500) wherein unreacted 2,2,4-trimethylpentane and 2,2,4-trimethylpentenes are removed overhead and sent through line (501) back to reactor (100).

The unvaporized products are withdrawn as liquid through line (502) and sent to a fractionating column (600) wherein toluene and benzene are removed overhead through line (601) and p-xylene, preferably of greater than 95% purity, is removed through line (602).

Those skilled in the art will recognize that since the drawings are representational, and additional equipment, such as pressure and temperature sensors, pressure relief and control valves, compressors, pumps, storage tanks, and the like, may be desired for a commercial plant. The provision of such ancillary items would be in accordance with conventional chemical engineering practice.

Without further elaboration, it is believed that one skilled in the art can, using the description herein, utilize the present invention to its fullest extent. The following embodiments are, therefore, to be construed as merely illustrative, and do not constrain the remainder of the disclosure in any way whatsoever.

EXAMPLES

General Procedure for Catalyst Testing

Catalyst tests were performed in a fixed-bed continuous-flow quartz reactor with 6.4 mm ID. The catalyst charge varied from 0.5 to 2.0 mL of −10/+60 mesh (−2.00/+0.25 mm) granules. The reactor tube was heated in a tube furnace to 500° C. in flowing nitrogen until the temperature was stable. A thermocouple inside the catalyst bed was used to measure temperature. Once the desired temperature was achieved, 2,2,4-trimethylpentane (TMP) was pumped and vaporized into the flowing nitrogen stream and passed over the catalyst bed for 5 minutes. Molar concentrations of TMP ranged from 10 to 50% with the balance being nitrogen. Contact times varied from 1 to 4 seconds. The entire product stream was analyzed on-line using sampling valves and an HP5890 chromatograph (TCD)/HP 5971 mass selective detector. After 5 minutes on stream, the feed was switched to $N_2$ only, to quickly purge, and then air was passed over the catalyst at a flow of about 100 cc/minute to burn coke off the catalyst surface. After air treatment, the catalyst was purged with $N_2$ before introducing TMP back into the stream for the next analysis.

The results of the catalyst tests are shown in Tables 1 and 2. For the examples shown in Tables 1 and 2 (Examples 1 to 28), the contact time was 1.6 seconds, the reaction temperature was 525° C., and the % TMP in the feed was 10%; the balance was nitrogen. (For Example 13 below, the balance was nitrogen (85%) and hydrogen (15%)). The catalyst charge was 2 mL for Examples 1 to 3, 5 to 19, 23, and 24. The catalyst charge was 1 mL for Examples 4, 20 to 22, and 25 to 28. The same catalyst and conditions were used for Examples 25 and 26. The results for Example 25 below represent the first pass over the catalyst.

| Legend | |
|---|---|
| Tmp is $(CH_3)_3CCH_2CH(CH_3)CH_3$ | iC4= is $(CH_3)_2C=CH_2$ |
| iC4 is $(CH_3)_2CHCH_3$ | Conv. is conversion |
| TMPE is a mixture of | |
| $(CH_3)_3CCH=C(CH_3)CH_3$ and | |
| $(CH_3)_3CCH_2C(C_3)=CH_2$ | |
| Sel. is selectivity | |

Example 1

KOH (5.9 g) and $CrO_3$ (55.5 g) were dissolved in distilled water (100 mL). To this solution was added Davison eta-alumina pellets (10 g) which were then soaked for six hours. After draining, the impregnated pellets were fired to 500° C. for six hours. Chemical analysis by inductively coupled plasma (ICP) of the pellets gave 1.53% K and 13.0% Cr.

Example 2

A 1 M aqueous solution of $Cr(NO_3)_3.9H_2O$ (53.263 mL) was added simultaneously with 0.1 M HCl (5.326 mL) to a 4.67 M preformed $AlO_{1.5}$ aquasol (11.41 mL) available from the Nyacol Corporation (Nyacol Al-20). The material appeared gel-like within minutes. It was dried under vacuum for 5 hours (120° C.) and dried and then calcined at 300° C. in air for 3 hours prior to use. The material was pelletized and granulated on −10/+20 mesh (−2.0/+0.84 mm) screens prior to use.

Examples 3 and 4

KOH (3.54 g) and $CrO_3$ (33.3 g) were dissolved in distilled water (60 mL). To this solution was added 7.5 g of UCI eta-alumina pellets which were then soaked for 21 hours. After draining, the impregnated pellets were fired to 500° C. for six hours in air. Chemical analysis by inductively coupled plasma (ICP) of the pellets gave 1.51% K and 12.0% Cr.

Examples 5 and 6

KOH (2.36 g) and $CrO_3$ (22.20 g) were dissolved in distilled water (20 mL). To this solution was added Davison eta-alumina pellets (10 g) which were then soaked for six hours at 75° C. After draining, the impregnated pellets were fired to 500° C. for six hours in air. Chemical analysis by inductively coupled plasma (ICP) of the pellets gave 1.97% K and 18.0% Cr.

Example 7

NaOH (0.42 g) and $CrO_3$ (5.55 g) were dissolved in distilled water (10 mL). To this solution was added United Catalysts Inc. (UCI) eta-alumina pellets (10 g) which were then soaked for 21 hours. After draining, the impregnated pellets were fired to 500° C. for six hours in air. Chemical analysis by inductively coupled plasma (ICP) of the pellets gave 1.09% Na and 16.8% Cr.

Examples 8 and 9

$CrO_3$ (8.325 g) was dissolved in distilled water (15 mL). To this solution was added UCI eta-alumina pellets (15 g) which were then soaked for 21 hours. After draining, the impregnated pellets were fired to 500° C. for six hours in air. A sample of the above pellets (5 g) was then soaked for three hours in a solution (1.60 g) of 50% by weight CsOH solution diluted to a total volume of 5 mL with distilled water. After draining, the impregnated pellets were fired to 500° C. for three hours in air. Chemical analysis by inductively coupled plasma (ICP) of the pellets gave 7.85% Cs and 5.77% Cr.

Example 10

$CrO_3$ (8.325 g) was dissolved in distilled water (15 mL). To this solution was added UCI eta-alumina pellets (15 g) which were then soaked for 21 hours. After draining, the impregnated pellets were fired to 500° C. for six hours in air. A sample (5 g) of the above pellets was then soaked for three hours in a solution (1.09 g) of a 50% by weight RbOH solution diluted to a total volume of 5 mL with distilled water. After draining, the impregnated pellets were fired to 500° C. for three hours in air. Chemical analysis by inductively coupled plasma (ICP) of the pellets gave 4.60% Rb and 10.4% Cr.

Example 11

$CrO_3$ (5.55 g) was dissolved in distilled water (10 mL). To this solution was added UCI eta-alumina pellets (10 g) which were then soaked for 21 hours. After draining, the impregnated pellets were fired to 500° C. for three hours in air. The pellets were then soaked for three hours in a solution of KOH (0.59 g) dissolved in distilled water (10 mL). After draining, the impregnated pellets were fired to 500° C. for three hours. Chemical analysis by inductively coupled plasma (ICP) of the pellets gave 2.28% K and 10.8% Cr.

Example 12

KOH (0.197 g), $Fe(NO_3)_3.9H_2O$ (0.709 g), and $CrO_3$ (1.932 g) were dissolved in distilled water (2.56 mL). To this solution was added UCI eta-alumina pellets (7.162 g) which were then tumbled on a rotary evaporator for 1 hour. Low heat and vacuum were then applied for sufficient time to completely dry the sample. The pellets were fired to 500° C. for six hours in air. Chemical analysis by inductively coupled plasma (ICP) of the pellets gave 1.45% K, 10.4% Cr, and 1.09% Fe.

Example 13

KOH (5.9 g) and $CrO_3$ (55.5 g) were dissolved in distilled water (100 mL). To this solution was added Davison eta-alumina pellets (10 g) which were then soaked for six hours at 75° C.. After draining, the impregnated pellets were fired to 500° C. for six hours in air. Chemical analysis by inductively coupled plasma (ICP) of the pellets gave 1.97% K and 18.0% Cr.

Example 14

A 1 M aqueous solution (36.033 mL) of $Cr(NO_3)_3 \cdot 9H_2O$ was added simultaneously with 0.1 M HCl (10.81 mL) to 4.67 M preformed $AlO_{1.5}$ aquasol (23.157 mL) available from the Nyacol corporation (Nyacol Al-20). The material became gel-like in appearance within minutes. It was dried under vacuum for 5 hours (120° C.) and calcined at 300° C. in air for 3 hours. The material was then pelletized and granulated on −10/+20 mesh (−2.0/+0.84 mm) screens prior to use.

Example 15

A 1.689 M (with respect to chromium) aqueous solution (81.72 mL) of $Cr_3(OH)_2(CH_3COO)_7$ was added to 118.28 mL of 4.68 M Nyacol Al-20 alumina colloid. A gel point was reached almost immediately. Ethanol (300 mL) was added to this material in order to exchange $H_2O$ (12 hours). The liquid layer was decanted from this mixture after 12 hours. Additional ethanol (400 mL) was added to the gel to allow it to further exchange with water; the material was exchanged overnight, and the top layer was decanted. The ethanol-containing gel was then supercritically dried according to the following procedure in a 1 liter autoclave: Heat for 4 hours to 330° C., 3345 PSIG (23.16 MPa); isotherm 1 hour at 330° C., approximately 3350 PSIG (23.19 MPa); vent while maintaining approximately 330° C. to atmospheric pressure. The free-flowing powder material was pelletized/granulated at 20,000 PSIG (138 MPa) and sieved on −10/+20 mesh (−2.0/+0.84 mm) screens prior to use.

Examples 16 and 17

A solution of chromium nitrate (19.0 g) dissolved in water (50 mL) was added to eta-alumina (10 g). The pH of the slurry was adjusted (with vigorous stirring) to 9.6 with 1 M sodium hydroxide solution, pausing between additions to assure the pH had stabilized before continuing. The eta-alumina and chromium hydrous oxide precipitate was kept at ambient temperature for 4 hours, then filtered and washed with distilled water (about 200 mL). The suction-dried solid was calcined at 250° C. in flowing air for 2 hours before use.

Example 18

A 2.56 M (with respect to chromium) aqueous solution (17.373 mL) of $Cr_3(OH)_2(CH_3COO)_7$ was added to 32.627 mL (2.045 M) of pre-formed $ZrO_2$ colloid (Nyacol, Zr 10/20). The mixture was dried at 120° C. in vacuum for 5 hours prior to use. It was pelletized at 20,000 PSIG (138 MPa) and granulated, −10/+20 mesh (−2.0/+0.84 mm) prior to use.

Example 19

$CrO_3$ (8.325 g) was dissolved in distilled water (15 mL). To this solution was added UCI eta-alumina pellets (15 g) which were then soaked for 21 hours. After draining, the impregnated pellets were fired to 500° C. for six hours in air. A sample (5 g) of the above pellets was then soaked for three hours in a solution (0.36 g) of $LiNO_3$ in distilled water (5 mL). After draining, the impregnated pellets were fired to 500° C. for three hours in air. Chemical analysis by inductively coupled plasma (ICP) of the pellets gave 0.18% Li and 11.5% Cr.

Example 20

A 0.1 M aqueous solution of $SnCl_4$ (1.276 mL) was added to 1.5 grams of a preformed and presieved/granulated K/Cr/eta-alumina catalyst prepared as described in Examples 3 and 4. The material was calcined at 375° C. for 3 hours in air prior to use.

Examples 21 and 22

A 0.136 M (with respect to tungsten) aqueous solution of $(NH_4)_{10}W_{12}O_{41} \cdot 5H_2O$ (0.6047 mL) was added to 1.5 g of preformed, pre-sieved/granulated K/Cr/eta-alumina catalyst prepared as described in Examples 3 and 4. The material was calcined at 375° C. for 3 hours in air prior to use.

Example 23

KOH (0.59 g), $CrO_3$ (5.0 g), and $La(NO_3)_3 \cdot 6H_2O$ (1.72 g) were dissolved in distilled water (10 mL). To this solution was added UCI eta-alumina pellets (10 g) which were then soaked for 24 hours at room temperature. After draining, the impregnated pellets were fired to 500° C. for three hours in air. Chemical analysis by inductively coupled plasma (ICP) of the pellets gave 1.27% K, 8.72% Cr, and 1.45% La.

Example 24

KOH (0.59 g), $CrO_3$ (5.0 g), and $Fe(NO_3)_3 \cdot 9H_2O$ (1.55 g) were dissolved in distilled water (10 mL). To this solution was added UCI eta-alumina pellets (10 g) which were then soaked for 24 hours at room temperature. After draining, the impregnated pellets were fired to 500° C. for three hours in air. Chemical analysis by inductively coupled plasma (ICP) of the pellets gave 1.45% K, 8.48% Cr and 0.80% Fe.

Examples 25 and 26

A 0.1 M aqueous $SnCl_4$ solution (0.126 mL) was added to 1.5 grams of preformed, presieved/granulated K/Cr/eta-alumina catalyst prepared as described in Examples 3 and 4. The material was calcined at 375° C. for 3 hours in air prior to use.

Example 27

$Cr(NO_3)_3 \cdot 9H_2O$ (49.80 g) was dissolved in a zirconyl nitrate solution (68.73 g, "20% $ZrO_2$") and water (18.37 g). Zirconium hydroxide (254.42 g) was mixed with methylcellulose (7.56 g). The solution was mixed with the powder to form a paste. The paste was extruded into ⅛" (3.2 mm) cylinders. After drying, the extrudates were heated slowly to 500° C. and held at that temperature for 4 hours. The extrudates were then crushed to between 40 and 60 mesh (0.42 mm to 0.25 mm) and slurried in a large excess of a 6% $KNO_3$ solution for 5 minutes. After filtering and drying, the granules were fired again at 500° C. for 4 hours before use.

Example 28

A 2.56 M (with respect to chromium) aqueous $Cr_3(OH)_2(CH_3CO_2)_7$ solution (3.906 mL) was added to 2.039 g of eta-alumina (Engelhard, SNL6469-30-1). The material was dried and calcined at 375° C. for 3 hours in air. The material was then granulated and sieved prior to use (−10/+20 mesh (−2.0/+0.84 mm)).

TABLE 1

| Ex. | % TMP Conv. | % Sel. iC4= | % Sel. iC4 | % Sel. Xylene[a] | % Sel. TMPE | % Sel. Others[b] |
|---|---|---|---|---|---|---|
| 1 | 84.72 | 28.68 | 13.67 | 29.32 | 21.78 | 6.55 |
| 2 | 9.14 | 66.96 | 0.00 | 21.54 | 0.00 | 11.50 |

TABLE 1-continued

| Ex. | % TMP Conv. | % Sel. iC4= | % Sel. iC4 | % Sel. Xylene[a] | % Sel. TMPE | % Sel. Others[b] |
|---|---|---|---|---|---|---|
| 3 | 80.69 | 31.95 | 10.30 | 27.88 | 20.47 | 9.40 |
| 4 | 66.09 | 29.71 | 6.07 | 26.69 | 32.46 | 5.07 |
| 5 | 83.93 | 30.42 | 11.77 | 29.21 | 24.53 | 4.06 |
| 6 | 80.65 | 29.75 | 9.85 | 27.97 | 28.99 | 3.44 |
| 7 | 80.45 | 32.02 | 9.59 | 29.36 | 20.31 | 8.72 |
| 8 | 83.34 | 27.06 | 9.14 | 25.58 | 22.81 | 15.42 |
| 9 | 83.64 | 27.12 | 9.22 | 25.07 | 22.87 | 15.72 |
| 10 | 83.02 | 25.81 | 9.61 | 26.06 | 22.25 | 16.27 |
| 11 | 72.53 | 25.79 | 6.23 | 21.65 | 27.94 | 18.39 |
| 12 | 76.68 | 28.00 | 6.74 | 21.72 | 21.69 | 21.85 |

[a]The p-xylene content of the xylenes is at least 95%.
[b]Others include primarily benzene and toluene.

TABLE 2

| Ex. | % TMP Conv. | % Sel. iC4= | % Sel. iC4 | % Sel. Xylene[a] | % Sel. TMPE | % Sel. Others[b] |
|---|---|---|---|---|---|---|
| 13 | 61.53 | 14.25 | 47.79 | 10.62 | 25.08 | 2.26 |
| 14 | 52.55 | 41.24 | 4.28 | 14.90 | 28.00 | 11.58 |
| 15 | 57.55 | 50.11 | 5.61 | 15.51 | 19.85 | 8.93 |
| 16 | 12.95 | 68.64 | 7.88 | 14.51 | 0.00 | 8.96 |
| 17 | 12.35 | 72.64 | 8.23 | 14.86 | 0.00 | 4.27 |
| 18 | 80.99 | 39.40 | 16.44 | 18.33 | 15.29 | 10.54 |
| 19 | 76.88 | 35.43 | 5.99 | 12.26 | 9.99 | 36.32 |
| 20 | 53.56 | 26.02 | 4.15 | 16.49 | 44.64 | 8.71 |
| 21 | 52.12 | 26.17 | 3.52 | 15.87 | 46.58 | 7.86 |
| 22 | 47.91 | 25.42 | 3.20 | 15.12 | 48.94 | 7.32 |
| 23 | 66.11 | 27.02 | 5.18 | 19.26 | 26.58 | 21.96 |
| 24 | 73.60 | 27.89 | 6.98 | 16.81 | 20.34 | 27.98 |
| 25 | 72.64 | 26.10 | 6.43 | 18.36 | 28.98 | 20.12 |
| 26 | 53.60 | 24.18 | 4.01 | 16.37 | 46.55 | 8.89 |
| 27 | 72.52 | 32.65 | 7.25 | 15.40 | 33.44 | 11.26 |
| 28 | 52.60 | 27.11 | 3.89 | 10.78 | 27.81 | 30.41 |

[a]The p-xylene content of the xylenes is at least 95%.
[b]Others include primarily benzene and toluene.

Example 29

Effect of Varying Isooctane Concentration on Yields to Desired Products

General Procedure for Catalyst Testing described above was used. The catalyst was 1.53% K/13.0% Cr/eta-alumina prepared as described in Example 1. TMP and nitrogen flow rates were changed to achieve the desired TMP concentrations. The contact time was 3.2 seconds, the reactor temperature was 500° C., and the time on stream before analysis was constant as the TMP concentrations were varied. The results are shown in Table 3.

TABLE 3

| % TMP Conc. | % Yield xylene[a] | % Yield iC4= | % Yield iC4 | % Yield TMPE | % Yield Others[b] |
|---|---|---|---|---|---|
| 10 | 30.1 | 30.0 | 22.2 | 5.6 | 8.6 |
| 20 | 24.4 | 26.4 | 21.1 | 8.4 | 6.0 |
| 30 | 17.4 | 21.2 | 16.7 | 9.9 | 16.1 |
| 40 | 15.2 | 20.5 | 15.9 | 11.1 | 13.8 |
| 50 | 12.1 | 19.5 | 12.9 | 12.5 | 11.0 |

[a]The p-xylene content of the xylenes is at least 95%.
[b]Others include primarily benzene and toluene.

Example 30

Signal Intensity Comparisons 10% TMP, 90% Diluent

The General Procedure for Catalyst Testing described above was used. The catalyst was 1.53% K/13.0% Cr/eta-alumina prepared as described in Example 1. The catalyst was heated up to 500° C. in nitrogen, then TMP was pumped and vaporized into the flowing nitrogen stream at the desired concentration. After 5 minutes on stream, reaction products were analyzed by gas chromatography (GC). Several analyses were completed under standard conditions. The TMP and xylene signal intensities obtained with $N_2$ as diluent were averaged and used to compare with signal intensities of TMP and p-xylene obtained when other diluents were used. Air recycle and nitrogen purge were used between each analysis.

| Diluent | TMP Area/TMP Area$_{N2}$ | xylene Area/xylene$_{N2}$ |
|---|---|---|
| Nitrogen | t | x |
| Methane | 1.05t | 0.96x |
| Ethane | 1.17t | 0.87x |
| Propane | 1.86t | 0.63x |
| Isobutane[a] | 3.73t | 0.51x |
| Butane[a] | 3.15t | 0.39x |

[a]Isobutane and butane are comparative examples.

TMP conversion was greater than 90% when nitrogen was used as the diluent. Therefore, intensities of greater than t indicate lower TMP conversion and intensities of less than x indicate lower xylene yields.

Example 31

Signal Intensity Comparisons 20% TMP, 80% Diluent

The same procedure as Example 30 was used except that the TMP concentration was 20%.

| Diluent | TMP Area/TMP Area$_{N2}$ | xylene Area/xylene$_{N2}$ |
|---|---|---|
| Nitrogen | t | x |
| Methane | 1.31t | 0.93x |
| Ethane | 1.30t | 0.90x |
| Propane | 1.47t | 0.71x |
| Isobutane[a] | 1.54t | 0.61x |
| Butane[a] | 1.35t | 0.50x |

[a]Isobutane and butane are comparative examples.

TMP conversion is greater than about 86% when nitrogen is used as the diluent. Therefore, intensities of greater than t indicate lower TMP conversion and intensities of less than x indicate lower xylene yields.

Comparative Example A

Use of Hydrogen as Diluent

The General Procedure for Catalyst Testing described above was used. The catalyst was 1.53% K/13.0% Cr/eta-alumina prepared as described in Example 1. The reaction temperature was 525° C. and the contact time was 1.6 seconds.

TABLE A

| Diluent | % TMP Conv. | % Sel. iC4= | % Sel. iC4 | % Sel. Xylene | % Sel. TMPE | % Sel. Others |
|---|---|---|---|---|---|---|
| $N_2$ | 82.3 | 28.6 | 12.7 | 28.9 | 24.6 | 5.4 |
| $H_2$ | 61.8 | 14.7 | 47.1 | 10.2 | 25 | 3.2 |

What is claimed is:

1. A process for the manufacture of xylene from 2,2,4-trimethylpentane, comprising:
    (a) feeding to a reactor a reactor feed comprising 2,2,4-trimethylpentane, and a diluent gas selected from the group consisting of nitrogen, methane, ethane, propane, and mixtures thereof wherein the molar concentration of 2,2,4-trimethylpentane to said diluent gas is about 50% or less;
    (b) contacting, in the vapor phase, said reactor feed with a catalyst comprising chromium to produce a reactor effluent containing xylene and by-products comprising 2,2,4-trimethylpentene, isobutane, isobutylene, and unreacted 2,2,4-trimethylpentane;
    (c) separating the isobutane and isobutylene from step (b) and passing said separated isobutane and isobutylene over an acid dimerization catalyst, at a temperature from about 5° C. to about 50° C., whereby the isobutane and isobutylene are dimerized to produce a mixture consisting essentially of trimethylpentane, trimethylpentene-1, and trimethylpentene-2, and, optionally, recycling said products to the reactor of step (a); and
    (d) optionally, separating xylene from said by-products, unreacted 2,2,4-trimethylpentane and diluent gas.

2. The process of claim 1 wherein the process further comprises separating the isobutane and isobutylene from step (b) and passing the separated isobutane and isobutylene over a bed of a dimerization catalyst in a separate reactor zone and dimerizing the isobutane and isobutylene.

3. The process of claim 1 wherein said catalyst is supported on an inorganic oxide selected from the group consisting of alumina, eta-alumina, and zirconia.

4. The process of claim 1 wherein the xylene of step (b) comprises greater than 95% p-xylene.

5. The process of claim 1 wherein said acid dimerization catalyst is hydrogen fluoride or sulfuric acid.

6. The process of claim 2 wherein the dimerization process is carried out at a temperature of about 150° C. to about 200° C., and a pressure from about 2000 kPa to about 5600 kPa, and a liquid hourly space velocity from about 3 to about 10.

7. The process of claim 1 wherein said catalyst is treated with a metal selected from the group consisting of iron, tin, and tungsten.

8. The process of claim 1 wherein said catalyst further comprises at least one metal selected from the group consisting of sodium, potassium, rubidium, cesium, magnesium, calcium, strontium, and barium.

9. The process of claim 1 wherein said catalyst comprises chromium and potassium supported on eta-alumina.

10. The process of claim 3 wherein said inorganic oxide is eta-alumina.

* * * * *